United States Patent
Sunahara et al.

(10) Patent No.: US 12,048,914 B2
(45) Date of Patent: Jul. 30, 2024

(54) DEODORIZING MATERIAL, METHOD FOR PRODUCING THE SAME, DEODORIZATION METHOD, AND DEODORIZING SHEET

(71) Applicant: UNITIKA LTD., Hyogo (JP)

(72) Inventors: Masao Sunahara, Kyoto (JP); Hiroki Fujiki, Kyoto (JP)

(73) Assignee: UNITIKA LTD. (JP)

( * ) Notice: Subject to any disclaimer, the term of this patent is extended or adjusted under 35 U.S.C. 154(b) by 827 days.

(21) Appl. No.: 17/040,674

(22) PCT Filed: Mar. 30, 2018

(86) PCT No.: PCT/JP2018/013519
§ 371 (c)(1),
(2) Date: Sep. 23, 2020

(87) PCT Pub. No.: WO2019/186986
PCT Pub. Date: Oct. 3, 2019

(65) Prior Publication Data
US 2021/0039067 A1    Feb. 11, 2021

(51) Int. Cl.
*B01J 20/22* (2006.01)
*A61L 9/014* (2006.01)
(Continued)

(52) U.S. Cl.
CPC ............... *B01J 20/22* (2013.01); *A61L 9/014* (2013.01); *B01J 20/20* (2013.01);
(Continued)

(58) Field of Classification Search
CPC .. A61L 9/104; B01J 20/20; B01J 20/22; B01J 20/28011; B01J 20/28023; B01J 20/2803;
(Continued)

(56) References Cited

U.S. PATENT DOCUMENTS 5,231,063 A * 7/1993 Fukumoto .......... B01J 20/28004
423/239.1
2015/0203678 A1    7/2015 Itoh et al.

FOREIGN PATENT DOCUMENTS

CN    101856890    10/2010
CN    104603195     7/2015
(Continued)

OTHER PUBLICATIONS

Machine Translation of "Fujiki H" (JP-2011072603-A), cited in IDS filed Sep. 23, 2020 (Year: 2011).*
(Continued)

*Primary Examiner* — Jennifer Wecker
*Assistant Examiner* — Brady C Pilsbury
(74) *Attorney, Agent, or Firm* — McDonald Hopkins LLC (57) ABSTRACT

There is provided a deodorizing material having particularly high deodorization capabilities for ammonia, acetaldehyde, and toluene. The deodorizing material of the present invention comprises fibrous activated carbon; and (A) an aromatic amine and a sulfate of the aromatic amine or (B) an aromatic amine, a sulfate of the aromatic amine, and sulfuric acid, supported on the fibrous activated carbon, wherein a total substance amount of the aromatic amine and the sulfate of the aromatic amine supported per gram of the fibrous activated carbon is 0.85 to 1.35 mmol, and a ratio of the total substance amount (mmol) of the aromatic amine and the sulfate of the aromatic amine supported per gram of the fibrous activated carbon relative to a total substance amount (mmol) of the sulfate of the aromatic amine and the sulfuric acid supported per gram of the fibrous activated carbon ([total substance amount of the aromatic amine and the sulfate of the aromatic amine]÷[total substance amount of the sulfate of the aromatic amine and the sulfuric acid]) is 5.0 to 7.5.

7 Claims, 3 Drawing Sheets

(51) Int. Cl.
*B01J 20/20* (2006.01)
*B01J 20/28* (2006.01)
*B01J 20/32* (2006.01)

(52) U.S. Cl.
CPC ... *B01J 20/28011* (2013.01); *B01J 20/28023* (2013.01); *B01J 20/2803* (2013.01); *B01J 20/3204* (2013.01); *B01J 20/3214* (2013.01); *B01J 20/3246* (2013.01); *B01J 20/3293* (2013.01)

(58) Field of Classification Search
CPC ............ B01J 20/3204; B01J 20/3214; B01J 20/3246; B01J 20/3293
See application file for complete search history.

(56) References Cited

FOREIGN PATENT DOCUMENTS

| | | |
|---|---|---|
| JP | 52063882 | 5/1977 |
| JP | 5023588 | 2/1993 |
| JP | 2004190144 A * | 7/2004 |
| JP | 2005152033 | 6/2005 |
| JP | 2011072603 | 4/2011 |
| WO | 2011040577 | 4/2011 |

OTHER PUBLICATIONS

Extended European Search Report mailed Oct. 19, 2021; European Patent Application No. 18913047.9.

Stevens et al., "Chemical Speciation and Bond Lengths of Organic Solutes by Core-Level Spectroscopy: PH and Solvent influence on p-Aminobenzoic Acid," Chemistry—A European Journal, vol. 21, No. 19 (Mar. 18, 2015), pp. 7256-7263.

State Intellectual Property Office of People's Republic of China, Notification of Office Action for Application No. 20201880091559.6, report issue date Oct. 25, 2021, China.

Patent Cooperation Treaty (PCT), International Search Report and Written Opinion for Application PCT/JP2018/013519 filed on Mar. 30, 2018, mailed Jun. 12, 2018, International Searching Authority, JP.

* cited by examiner

DEODORIZING MATERIAL, METHOD FOR PRODUCING THE SAME, DEODORIZATION METHOD, AND DEODORIZING SHEET

CROSS-REFERENCE TO RELATED APPLICATION

This application is a 35 U.S.C. 371 national stage filing of PCT Application No. PCT/JP2018/013519, filed on Mar. 30, 2018 which is incorporated herein in its entirety by reference.

TECHNICAL FIELD

The present invention relates to a deodorizing material, a method for producing the same, a deodorization method, and a deodorizing sheet.

BACKGROUND ART

In recent years, there has been a growing interest in air purification, and environments with reduced malodors have been required indoors or the like. Moreover, the problem of sick house syndrome has triggered a need for countermeasures against volatile organic compounds (VOCs) in residential environments.

For example, in the passenger compartment of a vehicle such as an automobile, malodors of volatile organic compounds from interior resin parts such as a seat pad, an instrument panel, and a door trim, coating materials, adhesives, and the like, as well as many malodors of exhaust gas, fuel odor, cigarettes, human bodies, rotten foods, and the like can be produced. In particular, the vehicle passenger compartment, which is a space narrower than a residence, is easily filled with such malodors when enclosed.

A deodorizing sheet for removing such malodors in a residential environment is known. For example, Patent Literature 1 discloses a deodorizing sheet mainly formed of fibrous activated carbon, comprising at least two types of fibrous activated carbon from acid gas-removing fibrous activated carbon, alkali gas-removing fibrous activated carbon, lower aldehyde-removing fibrous activated carbon, and hydrocarbon gas-adsorbing fibrous activated carbon. Patent Literature 1 describes that the deodorizing sheet achieves the effect of removing various odors by using a plurality of types of fibrous activated carbon that are specially processed for acid gas removal, alkali gas removal, lower aldehyde removal, and the like, as the fibrous activated carbon constituting the deodorizing sheet.

Patent Literature 2 discloses a fibrous deodorizing material comprising fibrous activated carbon, an aromatic amino acid, and sulfuric acid, which is intended to further improve the storage stability of the deodorizing sheet of Patent Literature 1 when it contains the lower aldehyde-removing fibrous activated carbon, while making the deodorizing sheet capable of removing the malodorous component at high efficiency. The fibrous deodorizing material is produced by a method comprising the following steps:

immersing fibrous activated carbon in an aqueous solution containing an aromatic amino acid and sulfuric acid, so that the aromatic amino acid and the sulfuric acid are supported on the fibrous activated carbon, wherein a mass ratio of the aromatic amino acid to the fibrous activated carbon is 10 to 20% by mass, and a mass ratio of the sulfuric acid to the fibrous activated carbon is 5 to 25% by mass;

removing the aqueous solution from the fibrous activated carbon on which the aromatic amino acid and the sulfuric acid are supported; and drying the fibrous activated carbon after removal of the aqueous solution.

CITATION LIST

Patent Literatures

Patent Literature 1: JP 2002-126511 A
Patent Literature 2: JP 2011-72603 A

SUMMARY OF INVENTION

Technical Problem

For example, the deodorizing sheet disclosed in Patent Literature 1 is expected to achieve the effect of removing various odors, because of the use of at least two of the four types of fibrous activated carbon as mentioned above. Research by the present inventor, however, has revealed that the deodorizing sheet disclosed in Patent Literature 1 may not be able to achieve a sufficient deodorization effect for certain odors. Specifically, it has been revealed that the deodorizing sheet disclosed in Patent Literature 1 may not be able to achieve a sufficient deodorization effect for ammonia and aldehyde, when it is produced using the alkali gas-removing fibrous activated carbon used for removing an alkali malodorous component such as ammonia, and using the lower aldehyde-removing fibrous activated carbon particularly used for removing a cigarette smell.

The fibrous deodorizing material disclosed in Patent Literature 2 has improved storage stability while being capable of removing the malodorous component at high efficiency, because it is obtained by immersing the fibrous activated carbon in an aqueous solution containing an aromatic amino acid and sulfuric acid in the above-mentioned specific ranges of proportions relative to the fibrous activated carbon. Research by the present inventor, however, has revealed that the fibrous deodorizing material disclosed in Patent Literature 2 may not be able to achieve a sufficient deodorization effect for ammonia and aldehyde, as in Patent Literature 1.

Moreover, because the countermeasures against volatile organic compounds (VOCs) in residential environments have been recently promoted, deodorizing materials have been required to have high deodorization capabilities for not only aldehyde compounds, such as formaldehyde and acetaldehyde, but also aromatic organic substances, such as toluene, that cannot be removed with an aromatic amino acid and sulfuric acid. In particular, in an environment inside a vehicle passenger compartment, besides aldehydes and aromatic organic substances, ammonia is produced by catalytic reduction treatment of nitrogen oxides included in exhaust gases, in an exhaust gas treatment apparatus. Thus, a deodorizing material used in a residential environment or an environment inside a vehicle passenger compartment has been required to remove aldehydes, aromatic organic substances, and ammonia in a balanced manner. Under such circumstances, it is a main object of the present invention to provide a deodorizing material having particularly high deodorization capabilities for acetaldehyde, toluene, and ammonia.

Solution to Problem

The inventor of the present invention has conducted extensive research to solve the aforementioned problem. As a result, the inventor has found that the following deodorizing material has particularly high deodorization capabilities for acetaldehyde, toluene, and ammonia; i.e., a deodorizing material comprising fibrous activated carbon; and (A) an aromatic amine and a sulfate of the aromatic amine or (B) an aromatic amine, a sulfate of the aromatic amine, and sulfuric acid, supported on the fibrous activated carbon, wherein a total substance amount of the aromatic amine and the sulfate of the aromatic amine supported per gram of the fibrous activated carbon is 0.85 to 1.35 mmol, and a ratio of the total substance amount (mmol) of the aromatic amine and the sulfate of the aromatic amine supported per gram of the fibrous activated carbon relative to a total substance amount (mmol) of the sulfate of the aromatic amine and the sulfuric acid supported per gram of the fibrous activated carbon ([total substance amount of the aromatic amine and the sulfate of the aromatic amine]÷[total substance amount of the sulfate of the aromatic amine and the sulfuric acid]) is 5.0 to 7.5. Specifically, the present inventor has found that a deodorizing material having high deodorization capabilities for all of three malodorous components, acetaldehyde, toluene, and ammonia, can be obtained by preparing a deodorizing material comprising fibrous activated carbon on which an aromatic amine and a sulfate of the aromatic amine are supported or a deodorizing material comprising fibrous activated carbon on which an aromatic amine, a sulfate of the aromatic amine, and sulfuric acid are supported; and further focusing on the following items that are not considered in Patent Literature 1 or 2, i.e., the total substance amount (mmol) of the aromatic amine and the sulfate of the aromatic amine supported on the fibrous activated carbon, and the ratio of the total substance amount (mmol) of the aromatic amine and the sulfate of the aromatic amine supported on the fibrous activated carbon relative to the total substance amount (mmol) of the sulfate of the aromatic amine and the sulfuric acid supported on the fibrous activated carbon ([total substance amount of the aromatic amine and the sulfate of the aromatic amine]÷[total substance amount of the sulfate of the aromatic amine and the sulfuric acid]), and then adjusting these items in the above-mentioned specific ranges. The present invention has been completed as a result of further research based on these findings.

In summary, the present invention provides the following aspects of the invention:

Item 1. A deodorizing material comprising fibrous activated carbon; and (A) an aromatic amine and a sulfate of the aromatic amine or (B) an aromatic amine, a sulfate of the aromatic amine, and sulfuric acid, supported on the fibrous activated carbon, wherein
  a total substance amount of the aromatic amine and the sulfate of the aromatic amine supported per gram of the fibrous activated carbon is 0.85 to 1.35 mmol, and
  a ratio of the total substance amount (mmol) of the aromatic amine and the sulfate of the aromatic amine supported per gram of the fibrous activated carbon relative to a total substance amount (mmol) of the sulfate of the aromatic amine and the sulfuric acid supported per gram of the fibrous activated carbon ([total substance amount of the aromatic amine and the sulfate of the aromatic amine]÷[total substance amount of the sulfate of the aromatic amine and the sulfuric acid]) is 5.0 to 7.5.

Item 2. The deodorizing material according to item 1, wherein p-aminobenzoic acid and a sulfate of p-aminobenzoic acid are supported on the fibrous activated carbon.

Item 3. A method for producing the deodorizing material according to item 1 or 2, comprising the step of immersing the fibrous activated carbon in a treatment liquid containing an aromatic amine and/or a salt thereof, sulfuric acid and/or a salt thereof, and water.

Item 4. A deodorization method for removing an odor of at least one selected from the group consisting of acetaldehyde, ammonia, and toluene, using the deodorizing material according to item 1 or 2.

Item 5. A deodorizing sheet comprising the deodorizing material according to item 1 or 2.

Item 6. The deodorizing sheet according to item 5, further comprising a binder.

Item 7. The deodorizing sheet according to item 5 or 6, wherein a density is 0.05 to 0.20 g/cm$^3$, and a thickness is 0.15 to 0.80 mm.

Advantageous Effects of Invention

The present invention can provide a deodorizing material having particularly high deodorization capabilities for acetaldehyde, toluene, and ammonia, and a deodorizing sheet including the deodorizing material.

DESCRIPTION OF EMBODIMENTS

A deodorizing material of the present invention comprises fibrous activated carbon; and (A) an aromatic amine and a sulfate of the aromatic amine or (B) an aromatic amine, a sulfate of the aromatic amine, and sulfuric acid, supported on the fibrous activated carbon, wherein a total substance amount of the aromatic amine and the sulfate of the aromatic amine supported per gram of the fibrous activated carbon is 0.85 to 1.35 mmol, and a ratio of the total substance amount (mmol) of the aromatic amine and the sulfate of the aromatic amine supported per gram of the fibrous activated carbon relative to a total substance amount (mmol) of the sulfate of the aromatic amine and the sulfuric acid supported per gram of the fibrous activated carbon ([total substance amount of the aromatic amine and the sulfate of the aromatic amine]÷[total substance amount of the sulfate of the aromatic amine and the sulfuric acid]) is 5.0 to 7.5. The deodorizing material of the present invention and a deodorizing sheet including the deodorizing material will be hereinafter described in detail.

The deodorizing material of the present invention comprises fibrous activated carbon; and (A) an aromatic amine and a sulfate of the aromatic amine or (B) an aromatic amine, a sulfate of the aromatic amine, and sulfuric acid. When the deodorizing material of the present invention comprises fibrous activated carbon, and an aromatic amine and a sulfate of the aromatic amine, the aromatic amine and the sulfate of the aromatic amine are supported on the fibrous activated carbon. Alternatively, when the deodorizing material of the present invention comprises fibrous activated carbon, and an aromatic amine, a sulfate of the aromatic amine, and sulfuric acid, the aromatic amine, the sulfate of the aromatic amine, and the sulfuric acid are supported on the fibrous activated carbon.

As used herein, "fibrous activated carbon" refers to activated carbon in the form of porous fibers having a high adsorption capability for organic substances and the like in a gas or a liquid, and refers to, for example, the activated carbon in the form of porous fibers as set forth in JIS K1477. The fibrous activated carbon is obtained by, for example, carbonizing a fiber produced using rayon, an acrylic fiber, a phenolic resin, pitch, or the like as a raw material, and then reacting (activating) the fiber with steam, carbon dioxide, or the like at a high temperature.

In the present invention, the fiber diameter of the fibrous activated carbon is not limited, but is preferably about 7 to 25 μm, and more preferably about 10 to 20 μm. The average fiber length of the fibrous activated carbon is not also limited, but is preferably 0.1 mm or more, and more preferably about 20 to 150 mm. The average fiber length of the fibrous activated carbon represents the value determined according to the method as set forth in JIS K1477. The specific surface area of the fibrous activated carbon is not also limited, but is preferably about 500 to 2000 $m^2/g$. The specific surface area of the fibrous activated carbon represents the value determined according to the BET method (one-point method) as set forth in JIS K1477.

While the aromatic amine is not limited in the present invention, it is preferably an aromatic amine in which a halogen, a sulfo group, an acetamide group, or a carbonyl group is attached to a benzene ring, in order to more effectively enhance the deodorization capabilities for acetaldehyde, toluene, and ammonia, and in view of safety and handleability during production. The aromatic amine in which a halogen, a sulfo group, an acetamide group, or a carbonyl group is attached to a benzene ring is preferably aminobenzoic acid, aminoacetanilide, aminosalicylic acid, or aminosulfanilic acid. In particular, aminobenzoic acid and a sulfate of aminobenzoic acid are preferred as the aromatic amine and the sulfate of the aromatic amine. That is, it is preferred that aminobenzoic acid and a sulfate thereof be supported on the fibrous activated carbon in the deodorizing material of the present invention. In the deodorizing material of the present invention, the aromatic amine at least partially forms a sulfate with the below-described sulfuric acid. A single aromatic amine and a sulfate of the aromatic amine may be used alone, or two or more aromatic amines and sulfates of the aromatic amines may be used in combination.

The aminobenzoic acid is not limited, and may be at least one selected from p-aminobenzoic acid, m-aminobenzoic acid, and o-aminobenzoic acid. It is particularly preferred that p-aminobenzoic acid be supported on the fibrous activated carbon in the deodorizing material of the present invention, in order to more effectively enhance the deodorization capabilities for acetaldehyde, toluene, and ammonia.

In the deodorizing material of the present invention, sulfuric acid may be supported together with the aromatic amine and the sulfate of the aromatic amine. That is, the deodorizing material of the present invention comprises fibrous activated carbon on which (A) an aromatic amine and a sulfate of the aromatic amine is supported (sulfuric acid may not be supported); or fibrous activated carbon on which (B) an aromatic amine, a sulfate of the aromatic amine, and sulfuric acid are supported.

Sulfuric acid has a relatively high boiling point, and does not easily volatilize. Because sulfuric acid promotes the dissolution of aminobenzoic acid in water, it allows the aromatic amine and the sulfate of the aromatic amine to be uniformly supported on the fibrous activated carbon, in the production process of the deodorizing material as described below. Sulfuric acid is also effective at inhibiting the polymerization of the aromatic amine and the sulfate of the aromatic amine in the deodorizing material.

As described above, for example, the deodorizing sheet disclosed in Patent Literature 1 is expected to achieve the effect of removing various odors, through selective use of the four types of fibrous activated carbon, i.e., alkali gas-removing fibrous activated carbon used for removing an alkali malodorous component such as ammonia, lower aldehyde-removing fibrous activated carbon particularly used for removing a cigarette smell, acid gas-removing fibrous activated carbon used for removing an acid malodorous component such as hydrogen sulfide, and hydrocarbon gas-adsorbing fibrous activated carbon. This deodorizing sheet, however, may not be able to achieve a sufficient deodorization effect for ammonia and aldehyde that are to be deodorized in the present invention, when, for example, the deodorizing sheet is produced using the alkali gas-removing fibrous activated carbon used for removing ammonia, and using the lower aldehyde-removing fibrous activated carbon for removing aldehydes.

Moreover, for example, the fibrous deodorizing material disclosed in Patent Literature 2, which is obtained by immersing fibrous activated carbon in an aqueous solution containing an aromatic amino acid and sulfuric acid in specific ranges of proportions relative to the fibrous activated carbon, may not also be able to achieve a sufficient deodorization effect for ammonia and aldehyde, as in Patent Literature 1.

In contrast, the deodorizing material of the present invention achieves high deodorization capabilities for all of three malodorous components, acetaldehyde, toluene, and ammonia, because it is obtained by preparing a deodorizing material comprising fibrous activated carbon on which an aromatic amine and a sulfate of the aromatic amine are supported or fibrous activated carbon on which an aromatic amine, a sulfate of the aromatic amine, and sulfuric acid are supported, and adjusting the total substance amount of the supported aromatic amine and sulfate of the aromatic amine to 0.85 to 1.35 mmol, preferably 0.90 to 1.35 mmol, per gram of the fibrous activated carbon excluding the aromatic amine, the sulfate of the aromatic amine, and the sulfuric acid, and further adjusting the ratio of the total substance amount (mmol) of the aromatic amine and the sulfate of the aromatic amine supported per gram of the fibrous activated carbon relative to the total substance amount (mmol) of the sulfate of the aromatic amine and the sulfuric acid supported per gram of the fibrous activated carbon ([total substance amount of the aromatic amine and the sulfate of the aromatic amine]÷[total substance amount of the sulfate of the aromatic amine and the sulfuric acid]) in the range of 5.0 to 7.5, preferably 5.3 to 7.5.

Although a detailed mechanism by which the deodorizing material of the present invention exhibits high deodorization capabilities for all the three malodorous components by adopting these specific features is not clear, the following factors are believed to be relevant: It is believed that in the deodorizing material comprising fibrous activated carbon on which an aromatic amine and a sulfate of the aromatic amine are supported, an aldehyde such as formaldehyde or acetaldehyde is removed mainly by the Schiff reaction with the supported aromatic amine, ammonia is removed mainly by the neutralization reaction with the supported sulfate of the aromatic amine or sulfuric acid, and an aromatic organic substance such as toluene is physically adsorbed mainly onto the micropores of the fibrous activated carbon, so that each component is deodorized. It is also believed that sulfuric acid serves to promote the reaction of an aromatic amine and an aldehyde, and also serves to inhibit the polymerization of the aromatic amine to maintain the reactivity. Meanwhile, if the supported amount of chemicals such as an aromatic amine and sulfuric acid increases, clogging of the micropores of the activated carbon will proceed, which adversely affects the deodorization effect for aromatic organic substances. In consideration of the above, it is believed that strict control of the supported amounts and the mixing ratio is required to realize the effect of deodorizing the three gases in a balanced manner, and because the total substance amount of the aromatic amine and sulfate of the aromatic amine supported on the deodorizing material, rather than the amount of the aromatic amine, sulfuric acid, and the like to be added to the below-described treatment liquid, is adjusted in the specific range, and then the ratio of the total substance amount (mmol) of the aromatic amine and the sulfate of the aromatic amine relative to the total substance amount (mmol) of the sulfate of the aromatic amine and the sulfuric acid is defined, factors responsible for a reduction in deodorization capability, such as the total substance amount of an aromatic amine and a sulfate of the aromatic amine, and additionally, clogging of the micropores in the deodorizing material, polymerization of an aromatic amine and a sulfate of the aromatic amine, and the like, are controlled, and consequently, the deodorizing material of the present invention exhibits a high deodorization effect for the three malodorous components.

In the deodorizing material of the present invention, the total substance amount of sulfuric acid (including the forms of salts, excluding a sulfate of an aromatic amine) is not limited as long as the ratio of the total substance amount (mmol) of the aromatic amine and the sulfate of the aromatic amine relative to the total substance amount (mmol) of the sulfate of the aromatic amine and the sulfuric acid falls in the above-mentioned range; for example, it is about 0.10 to 0.50 mmol, and preferably about 0.10 to 0.20 mmol, per gram of the fibrous activated carbon. The total substance amount of the aromatic amine and the sulfate of the aromatic amine, the total substance amount of the sulfate of the aromatic amine and the sulfuric acid, and the ratio of the total substance amount (mmol) of the aromatic amine and the sulfate of the aromatic amine relative to the total substance amount (mmol) of the sulfate of the aromatic amine and the sulfuric acid in the deodorizing material of the present invention may be measured, for example, as described below.

(Measurement of the Total Substance Amount of the Aromatic Amine and the Sulfate of the Aromatic Amine, and the Total Substance Amount of the Sulfate of the Aromatic Amine and the Sulfuric Acid)

The total substance amount of the aromatic amine and the sulfate of the aromatic amine supported on the fibrous activated carbon can be calculated by measuring the organic substance concentration in the liquid (below-described treatment liquid) before immersion of the fibrous activated carbon and the organic substance concentration in the liquid after immersion of the fibrous activated carbon, using a total organic carbon (TOC) analyzer, and determining the difference between the organic substance concentrations before and after the immersion operation. Specifically, using a total organic carbon (TOC) analyzer (TOC-5000 manufactured by Shimadzu Corporation), organic substance concentrations (mg C/L) in terms of carbon (C) are initially measured for the treatment liquid before and after the immersion operation, and the difference between the concentrations before and after the operation is determined. The resulting difference is multiplied by the treatment liquid volume (L), and the product is divided by {total atomic weight (g/mol) of total carbons in the aromatic amine×1000 (mg/g)} (for example, in the case of p-aminobenzoic acid or sulfate of p-aminobenzoic acid, the number of carbons is 7, and thus, the total atomic weight of total carbons is 84077 (mg/mol)). The resulting difference in the substance amount (mol) corresponds to the total substance amount (mol) of the aromatic amine and the sulfate of the aromatic amine supported on the fibrous activated carbon. If, in the organic substance concentration measurement, the concentration exceeds the upper limit of the detection limit of the total organic carbon (TOC) analyzer, then the treatment liquid may be diluted with a solvent, as appropriate, so that the concentration can be detected. The value of the organic substance concentration (mg C/L) is rounded to the nearest 0.1, in accordance with JIS Z 8401. Then, the thus-determined total supported amount (mol) of the aromatic amine and the sulfate of the aromatic amine is converted to mmol, and the result is divided by the mass (g) of the fibrous activated carbon before immersion in the treatment liquid. As a result, the total substance amount (mmol) of the aromatic amine and the sulfate of the aromatic amine per gram of the fibrous activated carbon as defined herein can be determined. The value of the substance amount (mmol) is herein rounded to the nearest 0.01, in accordance with JIS Z 8401.

Likewise, the total substance amount of the sulfate of the aromatic amine and the sulfuric acid supported on the fibrous activated carbon can be calculated by measuring the concentrations (mg/L) of sulfate ions in the liquid (below-described treatment liquid) before immersion of the fibrous activated carbon and in the liquid after immersion of the fibrous activated carbon, in accordance with the ion chromatography method as defined in JIS K 0101: 1998 42.4. Specifically, each of the sulfate ion concentrations (mg/L) in the treatment liquid before and after the immersion operation is measured using a calibration curve, and the difference between the concentrations (mg/L) before and after the operation is determined. The resulting difference between the concentrations (mg/L) before and after the operation is multiplied by the treatment liquid volume (L), and the product is divided by {sulfate ion molecular weight of 96.06 (g/mol)×1000 (mg/g)}, and the resulting difference in the substance amount (mol) of sulfate ions before and after the immersion operation corresponds to the total substance amount (mol) of the sulfate of the aromatic amine and the sulfuric acid supported on the fibrous activated carbon. The value of the sulfate ion concentration (mg/L) is rounded to the nearest 1, in accordance with JIS Z 8401. Then, the thus-determined total substance amount (mol) of the sulfate of the aromatic amine and the sulfuric acid supported on the fibrous activated carbon is converted to mmol, and the result is divided by the mass (g) of the fibrous activated carbon before immersion in the treatment liquid. As a result, the total substance amount (mmol) of the sulfate of the aromatic amine and the sulfuric acid per gram of the fibrous activated carbon can be determined.

(Ratio of the Total Substance Amount (mmol) of the Aromatic Amine and the Sulfate of the Aromatic Amine Relative to the Total Substance Amount (mmol) of the Sulfate of the Aromatic Amine and the Sulfuric Acid)

This ratio is calculated by dividing the total supported amount (mmol) of the aromatic amine and the sulfate of the aromatic amine supported per gram of the fibrous activated carbon, by the total supported amount (mmol) of the sulfate of the aromatic amine and the sulfuric acid supported per gram of the fibrous activated carbon, obtained by the measurement and calculation described above. The value of the ratio is rounded to the nearest 0.1, in accordance with JIS Z 8401.

The deodorizing material of the present invention (after (A) an aromatic amine and a sulfate of the aromatic amine or (B) an aromatic amine, a sulfate of the aromatic amine, and sulfuric acid are supported) has a specific surface area of about 500 to 1000 $m^2/g$, and preferably about 600 to 850 $m^2/g$. The specific surface area of the deodorizing material of the present invention represents the value determined according to the BET method (one-point method) as set forth in JIS K1477.

In the deodorizing material of the present invention, the equilibrium adsorption amount (mg/g ACF) of acetaldehyde at an equilibrium concentration of 10 ppm is preferably 45 mg/g ACF or more, more preferably 45 to 70 mg/g ACF, and particularly preferably 50 to 60 mg/g ACF. In the deodorizing material of the present invention, the equilibrium adsorption amount (mg/g ACF) of ammonia at an equilibrium concentration of 10 ppm is preferably 12 mg/g ACF or more, more preferably 12 to 20 mg/g ACF, and particularly preferably 12 to 15 mg/g ACF. In the deodorizing material of the present invention, the equilibrium adsorption amount (mg/g ACF) of toluene at an equilibrium concentration of 10 ppm is preferably 55 mg/g ACF or more, more preferably 55 to 90 mg/g ACF, and particularly preferably 55 to 80 mg/g ACF. The method for measuring the equilibrium adsorption amount of each of acetaldehyde, toluene, and ammonia at an equilibrium concentration of 10 ppm in the deodorizing material of the present invention is as follows:

(Measurement of the Equilibrium Adsorption Amount of Acetaldehyde)

A sample having a given weight and 3 L of 100-ppm acetaldehyde gas are sealed in a hermetically sealed container, and allowed to stand in an environment at 25° C. After a lapse of 24 hours, the gas concentration in the container is measured, and the adsorption amount is calculated. The measurement is conducted for a plurality of sample weights, and based on the results of calculation, the correlation between concentration and adsorption amount is plotted on a graph. From the relation thus obtained, the equilibrium adsorption amount (mg/g ACF) of acetaldehyde at the given equilibrium concentration is derived. The acetaldehyde concentration is measured using gas chromatography or a gas detector tube.

(Measurement of the Equilibrium Adsorption Amount of Ammonia)

Using ammonia instead of acetaldehyde, the equilibrium adsorption amount (mg/g ACF) of ammonia is determined as in the measurement of the equilibrium adsorption amount of acetaldehyde. The ammonia concentration is measured using ion chromatography or a gas detector tube.

(Measurement of the Equilibrium Adsorption Amount of Toluene)

Using toluene instead of acetaldehyde, the equilibrium adsorption amount (mg/g ACF) of toluene is determined as in the measurement of the equilibrium adsorption amount of acetaldehyde. The toluene concentration is measured using gas chromatography or a gas detector tube.

The deodorizing material of the present invention can be produced by, for example, as follows: Initially, a treatment liquid containing an aromatic amine and/or a salt thereof, sulfuric acid and/or a salt thereof, and water is prepared. The treatment solution may be prepared by dissolving the aromatic amine and/or its salt in an aqueous solution of the sulfuric acid and/or its salt diluted sufficiently with water, or by dissolving the aromatic amine and/or its salt in an aqueous solution containing the sulfuric acid and/or its salt at a relatively high concentration, and then diluting the solution with water. The sulfuric acid may be concentrated sulfuric acid or dilute sulfuric acid. To dissolve the aromatic amine and/or its salt in water, the aqueous solution of the sulfuric acid and/or its salt may be heated to a temperature of 50 to 80° C., for example, and the aromatic amine and/or its salt may be mixed into the heated solution. The aromatic amine to be supported on the deodorizing material of the present invention as described above is used as the aromatic amine. Examples of the salt of the aromatic amine include, but are not limited to, hydrochloride and sulfate of the aromatic amine.

The amount of the aromatic amine and/or its salt to be added to the treatment liquid is not limited as long as the supported amount of the aromatic amine and/or its salt in the deodorizing material of the present invention falls in the above-mentioned range; for example, it may be about 12 to 18 parts by mass per 100 parts by mass of the fibrous activated carbon to be immersed later. The amount of the sulfuric acid and/or its salt to be added to the treatment liquid is not limited as long as the contents and the ratio of the aromatic amine and the sulfate of the aromatic amine, or the aromatic amine, the sulfate of the aromatic amine, and the sulfuric acid fall in the above-mentioned ranges; for example, it may be about 12 to 18 parts by mass per 100 parts by mass of the fibrous activated carbon to be immersed later.

Subsequently, the fibrous activated carbon is immersed in the treatment liquid, so that the aromatic amine and the sulfate of the aromatic amine, or the aromatic amine, the sulfate of the aromatic amine, and the sulfuric acid are supported on the fibrous activated carbon. For example, the fibrous activated carbon is uniformly dispersed in the treatment solution, and then the dispersion is allowed to stand over a sufficient time. The time for immersing the fibrous activated carbon in the treatment liquid is about 1 hour or more, for example. The ratio of the mass of the fibrous activated carbon to the volume of the treatment liquid is in the range of 5 to 50 g/L, for example. If this ratio is excessively small, it will take a longer time for the aromatic amine and the sulfate of the aromatic amine, or the aromatic amine, the sulfate of the aromatic amine, and the sulfuric acid, to be supported on the fibrous activated carbon. Conversely, if this ratio is excessively large, it will be difficult for the aromatic amine and the sulfate of the aromatic amine, or the aromatic amine, the sulfate of the aromatic amine, and the sulfuric acid, to be uniformly supported on the fibrous activated carbon. If the time during which the fibrous activated carbon is contacted with the aqueous solution is sufficiently long, the effect of this ratio upon the amount of the aromatic amine and the sulfate of the aromatic amine, or the amount of the aromatic amine, the sulfate of the aromatic amine, and the sulfuric acid, to be supported on the fibrous activated carbon, can become negligible. The treatment liquid in which the fibrous activated carbon is to be immersed may be used in a heated state as it is heated during the addition of the aromatic amine and/or its salt, or may be used after the heated treatment liquid is cooled.

Subsequently, the treatment liquid is removed from the fibrous activated carbon on which the aromatic amine and the sulfate of the aromatic amine, or the aromatic amine, the sulfate of the aromatic amine, and the sulfuric acid are supported. The method for removing the treatment liquid is not limited; for example, the fibrous activated carbon may be withdrawn from the treatment liquid. The treatment liquid may be diluted with water, prior to the removal of the treatment liquid from the fibrous activated carbon on which the aromatic amine and the sulfate of the aromatic amine, or the aromatic amine, the sulfate of the aromatic amine, and the sulfuric acid are supported.

Thereafter, the fibrous activated carbon from which the treatment liquid has been removed is dried. The drying may be performed using, for example, natural drying, draft drying, hot-air drying, microwave heating drying, or indirect heating drying. The drying is performed so that the temperature of the fibrous activated carbon is maintained at, for example, 130° C. or lower, preferably 80° C. or lower. The deodorizing material of the present invention can be produced as described above.

The deodorizing sheet of the present invention will be described in detail next. The deodorizing sheet of the present invention is obtained using the deodorizing material of the present invention described above, and includes the deodorizing material of the present invention. Specifically, the deodorizing sheet of the present invention is obtained by molding the deodorizing material into a sheet. The sheet is preferably in the form of a nonwoven fabric, although not limited thereto. The deodorizing sheet of the present invention may optionally include a binder for the purpose of, for example, molding the deodorizing material into a sheet. The binder is not limited as long as it can bond the fibrous activated carbon constituting the deodorizing material; for example, the binder may be a fibrous binder, and commercially available fibrous binders include trade name MELTY manufactured by UNITIKA LTD.

When the deodorizing sheet of the present invention includes a binder, the mass ratio of the binder to the fibrous activated carbon on which the aromatic amine and the sulfate of the aromatic amine, or the aromatic amine, the sulfate of the aromatic amine, and the sulfuric acid are supported (binder/fibrous activated carbon) is preferably about 75/25 to about 25/75. When the deodorizing sheet has a low density as described above, even higher deodorization capabilities for ammonia, acetaldehyde, and toluene can be achieved, and thus, the mass proportion of the expensive fibrous activated carbon can be readily reduced. In this case, for example, the mass ratio of the binder to the fibrous activated carbon on which the aromatic amine and the sulfate of the aromatic amine, or the aromatic amine, the sulfate of the aromatic amine, and the sulfuric acid are supported (binder/fibrous activated carbon) can be readily reduced to about 75/25 to about 65/35.

While the density of the deodorizing sheet of the present invention is not limited, it is, for example, preferably 0.05 to 0.3 g/cm$^3$, more preferably 0.05 to 0.20 g/cm$^3$, and particularly preferably 0.08 to 0.12 g/cm$^3$, in order to achieve even higher deodorization capabilities for ammonia, acetaldehyde, and toluene. The thickness of the deodorizing sheet of the present invention is, for example, 0.15 to 0.80 mm or 0.15 to 0.50 mm, and preferably 0.15 to 0.25 mm, so that the deodorizing sheet can be readily housed in the cover of a seat in a vehicle passenger compartment, while achieving the high deodorization capabilities. The sheet having a low density and/or a small thickness as described above can be obtained by, for example, producing a thin nonwoven fabric having a basis weight of about 1 to 8 g/m$^2$, placing a plurality of layers of the nonwoven fabric on one another, and integrating the layered nonwoven fabric by needle punching.

The deodorizing sheet of the present invention can be produced by, for example, molding the deodorizing material into a sheet. Alternatively, the deodorizing sheet can be produced by molding the fibrous activated carbon before an aromatic amine and a sulfate of the aromatic amine, or an aromatic amine, a sulfate of the aromatic amine, and sulfuric acid are supported thereon into a sheet, and then immersing the sheet in the treatment liquid as described above, so that the aromatic amine and the sulfate of the aromatic amine, or the aromatic amine, the sulfate of the aromatic amine, and the sulfuric acid are supported on the fibrous activated carbon.

When the deodorizing sheet of the present invention is used as an air-purifying sheet, it may be provided as a layered structure having a dust-removing effect, by bonding a dust-removing sheet, such as an electret nonwoven fabric sheet, an HEPA (High-Efficiency Particulate Air) filter, or a ULPA (Ultra-Low Penetration Air) filter, to the deodorizing sheet. Such a layered structure can be suitably used for an air purifier that performs air purification and dust removal.

The deodorizing sheet of the present invention, which includes the deodorizing material of the present invention described above, can remove ammonia, acetaldehyde, and toluene from a gaseous phase at high efficiency. Therefore, the deodorizing sheet of the present invention can be extensively used in residential environments, and can also be suitably used for interior materials for automobiles, trains, ships, airplanes, and the like. In particular, the deodorizing sheet of the present invention can be housed in the cover of a seat in a vehicle passenger compartment and used as an automotive interior material that removes ammonia, acetaldehyde, and toluene from a gaseous phase at high efficiency. That is, a seat for a vehicle passenger compartment that includes the deodorizing sheet of the present invention can be provided. The deodorizing material of the present invention also has deodorization capabilities for lower aldehydes other than acetaldehyde, such as formaldehyde, and aromatic organic substances other than toluene, such as benzene, o-xylene, m-xylene, p-xylene, ethylbenzene, and styrene.

EXAMPLES

The present invention will be hereinafter described in detail with reference to examples and comparative examples; however, the present invention is not limited to the examples.

(Examples 1 to 3 and Comparative Examples 1 to 6)

An aqueous solution of sulfuric acid containing sulfuric acid at a concentration of 75% by mass was prepared. The aqueous solution of sulfuric acid was stirred at a temperature of 65° C. or higher, and p-aminobenzoic acid was added to the aqueous solution and completely dissolved. Then, water was added so that the ratio of the mass of fibrous activated carbon to the volume of treatment liquid was 20 g/L. As a result, a treatment liquid was obtained. The amounts (parts by mass) of sulfuric acid and p-aminobenzoic acid added in each of Examples 1 to 3 and Comparative Examples 1 to 6 are as shown in Table 1. The amount (parts by mass) of sulfuric acid shown in the table represents the amount (parts by mass) of sulfuric acid alone in the 75% aqueous solution of sulfuric acid, excluding pure water.

Subsequently, 100 parts by mass of fibrous activated carbon was immersed in the treatment liquid. The fibrous activated carbon was AD'ALL A-10 manufactured by UNITIKA LTD., i.e., pitch-based fibrous activated carbon having a specific surface area of 1260 m$^2$/g. This solution was then stirred over 10 minutes to allow the fibrous activated carbon to be uniformly dispersed in the solution. Thereafter, the dispersion was allowed to stand. After the dispersion was allowed to stand for 8 hours or more, the fibrous activated carbon was withdrawn from the solution, and dried at 80° C. with a dryer over 3 hours to obtain a deodorizing material of each of Examples 1 to 3 and Comparative Examples 1 to 6. The supported amounts of p-aminobenzoic acid and sulfuric acid, the molar ratio between the supported p-aminobenzoic acid and sulfuric acid, and the equilibrium adsorption amounts of acetaldehyde, ammonia, and toluene in each of the deodorizing materials, as well as the specific surface area of the deodorizing material, were each measured as follows:
(Measurement of the Total Supported Amount (mmol) of the Aromatic Amine and the Sulfate of the Aromatic Amine Supported per Gram of the Fibrous Activated Carbon, and the Total Supported Amount (mmol) of the Sulfate of the Aromatic Amine and the Sulfuric Acid Supported per Gram of the Fibrous Activated Carbon)

Using the method described in the (Measurement of the Total Supported Amount of the Aromatic Amine and the Sulfate of the Aromatic Amine, and the Total Supported Amount of the Sulfate of the Aromatic Amine and the Sulfuric Acid) section above, these total supported amounts were measured for each of the deodorizing materials of Examples 1 to 3 and Comparative Examples 1 to 6. The results are shown in Table 1. In the measurement, the activated carbon was used in an amount of 2.0 g, and the treatment liquid volume was adjusted to 100 ml by adding pure water as the balance.
(Ratio of the Total Substance Amount (mmol) of the Aromatic Amine and the Sulfate of the Aromatic Amine Supported per Gram of the Fibrous Activated Carbon Relative to the Total Substance Amount (mmol) of the Sulfate of the Aromatic Amine and the Sulfuric Acid Supported per Gram of the Fibrous Activated Carbon)

Using the method described in the (Ratio of the Total Substance Amount (mmol) of the Aromatic Amine and the Sulfate of the Aromatic Amine Relative to the Total Substance Amount (mmol) of the Sulfate of the Aromatic amine and the Sulfuric Acid) section described above, the ratio of the total substance amount (mmol) of the aromatic amine and the sulfate of the aromatic amine supported per gram of the fibrous activated carbon relative to the total substance amount (mmol) of the sulfate of the aromatic amine and the sulfuric acid supported per gram of the fibrous activated carbon was measured for each of the deodorizing materials of Examples 1 to 3 and Comparative Examples 1 to 6. The results are shown in Table 1. In the measurement, the activated carbon was used in an amount of 2.0 g, and the treatment liquid volume was adjusted to 100 ml by adding pure water as the balance.
(Equilibrium Adsorption Amount of Acetaldehyde)

Using the method described in the "Measurement of the Equilibrium Adsorption Amount of Acetaldehyde" section described above, the equilibrium adsorption amount (mg/g ACF) of acetaldehyde at an equilibrium concentration of 10 ppm was measured for each of the deodorizing materials of Examples 1 to 3 and Comparative Examples 1 to 6. The results are shown in Table 2.
(Equilibrium Adsorption Amount of Ammonia)

Using ammonia instead of acetaldehyde, the equilibrium adsorption amount (mg/g ACF) of ammonia was determined as in the measurement of the equilibrium adsorption amount of acetaldehyde. The results are shown in Table 2.
(Equilibrium Adsorption Amount of Toluene)

Using toluene instead of acetaldehyde, the equilibrium adsorption amount (mg/g ACF) of toluene was determined as in the measurement of the equilibrium adsorption amount of acetaldehyde. The results are shown in Table 1.
(Specific Surface Area of Deodorizing Material)

The specific surface area of each deodorizing material was determined using the BET method (one-point method). The results are shown in Table 2.

TABLE 1

| | | Aromatic Amine and Sulfate of the Aromatic Amine | | | Sulfuric Acid and Sulfate of the Aromatic Amine | |
|---|---|---|---|---|---|---|
| | amount (parts by mass) of PABA added per 100 parts by mass of the activated carbon | TOC measurement value (mg C/L) in the treatment liquid before the treatment at 2 g of the activated carbon/100 mL | TOC measurement value (mg C/L) in the treatment liquid after the treatment at 2 g of the activated carbon/100 mL | total substance amount A (mmol) of the aromatic amine and the sulfate of the aromatic amine supported per gram of the fibrous activated carbon | amount (parts by mass) of sulfuric acid added per 100 parts by mass of the activated carbon | sulfate ion measurement value (mg C/L) before the treatment at 2 g of the activated carbon/100 mL |
| Example1 | 15.0 | 1877.0 | 46.5 | 1.09 | 15.0 | 3713 |
| Example2 | 13.0 | 1622.8 | 39.3 | 0.94 | 15.0 | 3713 |
| Example3 | 18.0 | 2251.5 | 54.3 | 1.31 | 15.0 | 3713 |
| Comparative Example1 | 10.0 | 1255.3 | 32.2 | 0.73 | 15.0 | 3713 |
| Comparative Example2 | 15.0 | 1880.2 | 46.4 | 1.09 | 7.5 | 1864 |
| Comparative Example3 | 15.0 | 1881.3 | 46.1 | 1.09 | 37.5 | 9255 |
| Comparative Example4 | 15.0 | 1876.2 | 46.3 | 1.09 | 11.3 | 2803 |
| Comparative Example5 | 10.0 | 1254.1 | 33.5 | 0.73 | 16.9 | 4155 |
| Comparative Example6 | 20.0 | 2503.5 | 58.4 | 1.45 | 16.9 | 4155 |

TABLE 1-continued

| | Sulfuric Acid and Sulfate of the Aromatic Amine | | | |
|---|---|---|---|---|
| | sulfate ion measurement value (mg C/L) after the treatment at 2 g of the activated carbon/100 mL | total substance amount B (mmol) of the sulfate of the aromatic amine and the sulfuric acid supported per gram of the fibrous activated carbon | A/B | Specific Surface Area (m²/g) |
| Example1 | 3380 | 0.17 | 6.4 | 716 |
| Example2 | 3381 | 0.17 | 5.5 | 790 |
| Example3 | 3359 | 0.18 | 7.3 | 670 |
| Comparative Example1 | 3399 | 0.16 | 4.6 | 839 |
| Comparative Example2 | 1706 | 0.08 | 13.6 | 753 |
| Comparative Example3 | 8392 | 0.45 | 2.4 | 608 |
| Comparative Example4 | 2547 | 0.13 | 8.4 | 735 |
| Comparative Example5 | 3802 | 0.18 | 4.1 | 800 |
| Comparative Example6 | 3763 | 0.20 | 7.3 | 580 |

In Table 1, PABA denotes p-aminobenzoic acid.

TABLE 2

| | Equilibrium Adsorption Amounts (mg/g of Activated Carbon) of Gases | | |
|---|---|---|---|
| | Acetaldehyde | Ammonia | Toluene |
| Example1 | 57.2 | 13.2 | 59.3 |
| Example2 | 50.3 | 13.2 | 73.1 |
| Example3 | 54.2 | 13.2 | 58.7 |
| Comparative Example1 | 40.0 | 13.2 | 79.2 |
| Comparative Example2 | 59.7 | 9.9 | 68.2 |
| Comparative Example3 | 43.2 | 15.8 | 54.6 |
| Comparative Example4 | 58.5 | 11.6 | 66.4 |
| Comparative Example5 | 38.9 | 14.0 | 74.4 |
| Comparative Example6 | 48.5 | 13.9 | 48.5 |

As shown in Table 2, for the deodorizing materials of Examples 1 to 3 in which the total substance amount of p-aminobenzoic acid and the sulfate of p-aminobenzoic acid supported per gram of the fibrous activated carbon was 0.85 to 1.35 mmol, and the ratio of the total substance amount (mmol) of p-aminobenzoic acid and the sulfate of p-aminobenzoic acid supported per gram of the fibrous activated carbon relative to the total substance amount (mmol) of the sulfate of p-aminobenzoic acid and sulfuric acid supported per gram of the fibrous activated carbon was in the range of 5.0 to 7.5, the equilibrium adsorption amounts of all of acetaldehyde, ammonia, and toluene at a concentration of 10 ppm were large.

On the other hand, for the deodorizing material of Comparative Example 1 in which the total substance amount of p-aminobenzoic acid and the sulfate of p-aminobenzoic acid supported per gram of the fibrous activated carbon was as small as 0.73 mmol, and the ratio of the total substance amount (mmol) of p-aminobenzoic acid and the sulfate of p-aminobenzoic acid supported per gram of the fibrous activated carbon relative to the total substance amount (mmol) of the sulfate of p-aminobenzoic acid and sulfuric acid supported per gram of the fibrous activated carbon was as small as 4.6, although the equilibrium adsorption amounts of ammonia and toluene at a concentration of 10 ppm were large, the equilibrium adsorption amount of acetaldehyde at a concentration of 10 ppm was small.

For the deodorizing material of Comparative Example 2 in which the ratio of the total substance amount (mmol) of p-aminobenzoic acid and the sulfate of p-aminobenzoic acid supported per gram of the fibrous activated carbon relative to the total substance amount (mmol) of the sulfate of p-aminobenzoic acid and sulfuric acid supported per gram of the fibrous activated carbon was as large as 13.6, although the equilibrium adsorption amounts of acetaldehyde and toluene at a concentration of 10 ppm were large, the equilibrium adsorption amount of ammonia at a concentration of 10 ppm was small.

For the deodorizing material of Comparative Example 3 in which the ratio of the total substance amount (mmol) of p-aminobenzoic acid and the sulfate of p-aminobenzoic acid supported per gram of the fibrous activated carbon relative to the total substance amount (mmol) of the sulfate of p-aminobenzoic acid and sulfuric acid supported per gram of the fibrous activated carbon was 2.4, which was even smaller than that of Comparative Example 1, although the equilibrium adsorption amount of ammonia at a concentration of 10 ppm was considerably large, the equilibrium adsorption amount of acetaldehyde at a concentration of 10 ppm was small.

For the deodorizing material of Comparative Example 4 in which the amount of p-aminobenzoic acid added was 15.0 parts by mass, and the amount of sulfuric acid added was 11.3 parts by mass, per 100 parts by mass of the fibrous activated carbon, which were similar to the proportions used in Example 10 of Patent Literature 2, the ratio of the total substance amount (mmol) of p-aminobenzoic acid and the sulfate of p-aminobenzoic acid supported per gram of the fibrous activated carbon relative to the total substance amount (mmol) of the sulfate of p-aminobenzoic acid and sulfuric acid supported per gram of the fibrous activated carbon was as large as 8.4, and consequently, the equilibrium adsorption amount of ammonia at a concentration of 10 ppm was small.

For the deodorizing material of Comparative Example 5 in which the amount of p-aminobenzoic acid added was 10.0 parts by mass, and the amount of sulfuric acid added was 16.9 parts by mass, per 100 parts by mass of the fibrous activated carbon, which were similar to the proportions used in Example 3 of Patent Literature 2, the supported amount of p-aminobenzoic acid was as small as 10.0 parts by mass, and the ratio of the total substance amount (mmol) of p-aminobenzoic acid and the sulfate of p-aminobenzoic acid supported per gram of the fibrous activated carbon relative to the total substance amount (mmol) of the sulfate of p-aminobenzoic acid and sulfuric acid supported per gram of the fibrous activated carbon was as small as 4.1, and consequently, the equilibrium adsorption amount of acetaldehyde at a concentration of 10 ppm was small.

For the deodorizing material of Comparative Example 6 in which the amount of p-aminobenzoic acid added was 20.0 parts by mass, and the amount of sulfuric acid added was 16.9 parts by mass, per 100 parts by mass of the fibrous activated carbon, which were similar to the proportions used in Example 7 of Patent Literature 2, the total substance amount of p-aminobenzoic acid and the sulfate of p-aminobenzoic acid was as large as 1.45 mmol/g, and consequently, the equilibrium adsorption amounts of acetaldehyde and toluene at a concentration of 10 ppm were small.

(Production of Deodorizing Sheets)

Example 4

The deodorizing material obtained in Example 1 and a binder fiber (trade name MELTY 4080 manufactured by UNITIKA LTD.) were blended at a mass ratio (binder/deodorizing material) of 70/30 to produce a nonwoven fabric having a basis weight of 2 g/m². Ten sheets of the nonwoven fabric were placed on one another and then needle-punched, and the nonwoven fabric was heated at a temperature of 110° C. to melt the binder fiber, so that the binder fiber and the deodorizing material were fused, thus obtaining a deodorizing sheet having a thickness of 0.2 mm and a density of 0.1 g/m³. The deodorizing material in the deodorizing sheet for evaluation had a basis weight of 6 g/m².

Example 5

The deodorizing material obtained in Example 1 and a binder fiber (trade name MELTY 4080 manufactured by UNITIKA LTD.) were blended at a mass ratio (binder/deodorizing material) of 30/70 to produce a nonwoven fabric having a basis weight of 6 g/m². Ten sheets of the nonwoven fabric were placed on one another and then needle-punched, and the nonwoven fabric was heated at a temperature of 110° C. to melt the binder fiber, so that the binder fiber and the deodorizing material were fused, thus obtaining a deodorizing sheet having a thickness of 0.4 mm and a density of 0.15 g/m³. The deodorizing sheet was used as is for evaluation. The deodorizing material in the deodorizing sheet for evaluation had a basis weight of 42 g/m².

(Evaluation of the Capabilities of the Deodorizing Sheets)

Figure 1:
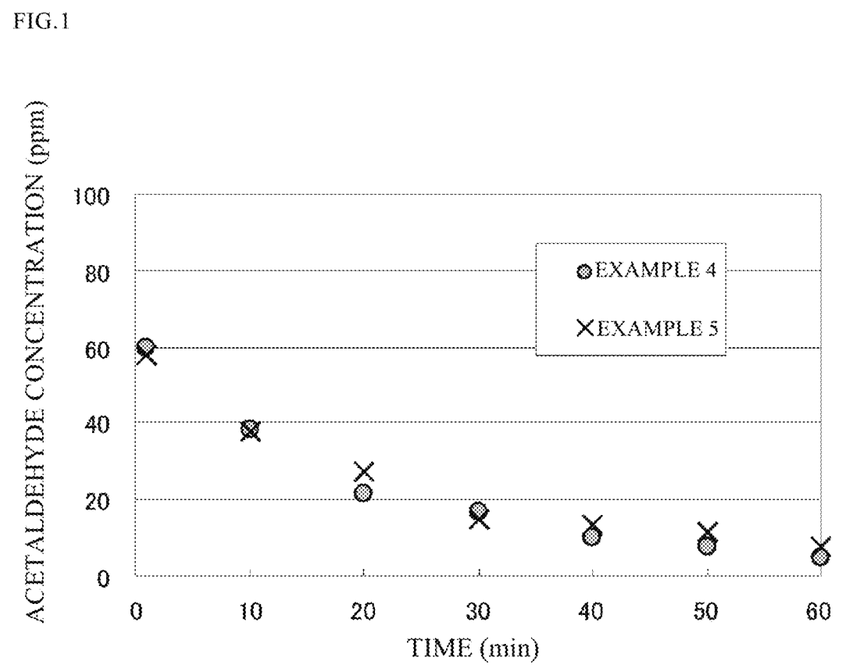
FIG. 1 is a graph showing the relationship between the acetaldehyde concentration and time in examples.

Each of the deodorizing sheets obtained in Examples 4 and 5 was cut into a size of 40 mm×50 mm and sealed in a gas bag having an acetaldehyde concentration of 100 ppm, a relative humidity of 50%, and a temperature of 40° C. The acetaldehyde concentration in the gas bag was measured after a lapse of 1, 10, 20, 30, 40, 50, or 60 minutes, and the acetaldehyde adsorption capacity of the deodorizing sheet was evaluated. The acetaldehyde concentration was measured using gas chromatography. For Example 4, five pieces of the deodorizing sheet cut into a size of 40 mm×50 mm were sealed in, and the measurement was conducted; and for Example 5, one piece of the deodorizing sheet cut into a size of 40 mm×50 mm was sealed in, and the measurement was conducted. The results are shown in Table 3. The relationship between the acetaldehyde concentration and time is illustrated in FIG. 1.

Figure 2:
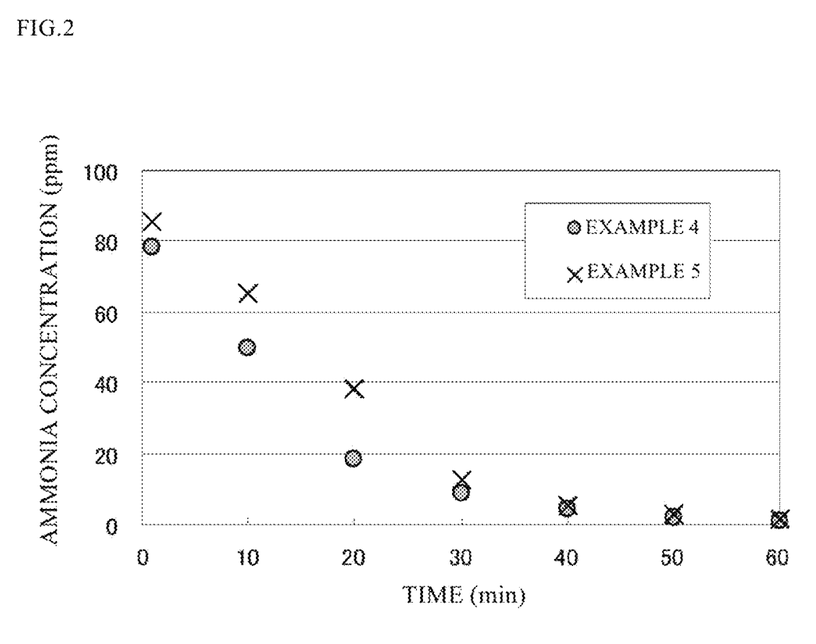
FIG. 2 is a graph showing the relationship between the ammonia concentration and time in examples.

Using ammonia instead of acetaldehyde, the ammonia adsorption capacity of each deodorizing sheet was evaluated as in the measurement of the acetaldehyde adsorption capacity of the deodorizing sheet. The results are shown in Table 3. The relationship between the ammonia concentration and time is illustrated in FIG. 2.

Using toluene instead of acetaldehyde, the toluene adsorption capacity of each deodorizing sheet was evaluated as in the measurement of the acetaldehyde adsorption capacity of the deodorizing sheet. The results are shown in Table 3. The relationship between the toluene concentration and time is illustrated in FIG. 3.

TABLE 3

| Gas Species | Time (min) | Example 4 Concentration (ppm) | Example 5 Concentration (ppm) |
|---|---|---|---|
| Acetaldehyde | 1 | 60.0 | 58.0 |
|  | 10 | 38.2 | 37.8 |
|  | 20 | 21.7 | 27.3 |
|  | 30 | 16.7 | 15.0 |
|  | 40 | 10.0 | 13.3 |
|  | 50 | 7.5 | 11.7 |
|  | 60 | 5.0 | 7.5 |
| Ammonia | 1 | 78.5 | 85.5 |
|  | 10 | 50.0 | 65.0 |
|  | 20 | 18.5 | 38.0 |
|  | 30 | 8.8 | 12.5 |
|  | 40 | 4.5 | 5.4 |
|  | 50 | 2.0 | 2.8 |
|  | 60 | 1.2 | 1.5 |
| Toluene | 1 | 40.0 | 40.0 |
|  | 10 | 10.7 | 25.0 |
|  | 20 | 3.0 | 14.5 |
|  | 30 | 2.0 | 7.1 |
|  | 40 | 2.0 | 4.6 |
|  | 50 | 1.0 | 2.0 |
|  | 60 | 1.0 | 1.0 |

Figure 3:
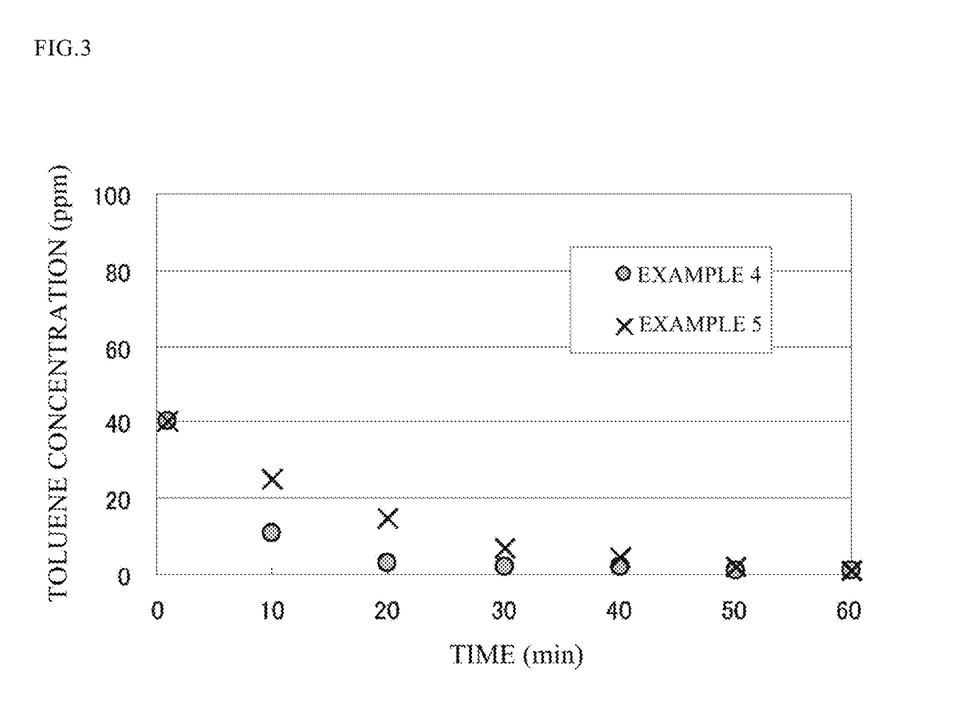
FIG. 3 is a graph showing the relationship between the toluene concentration and time in examples.

As shown in Table 3 and in FIGS. 1 to 3, the deodorizing sheets of Examples 4 and 5, both including the deodorizing material of the present invention, were confirmed to have particularly high deodorization capabilities for ammonia, acetaldehyde, and toluene. In particular, the deodorizing sheet of Example 4 had a density of 0.08 to 0.12 g/cm³ and a thickness of 0.15 to 0.25 mm, so that the total basis weight of the deodorizing material of the present invention in the five pieces cut from the deodorizing sheet of Example 4 was 30 g/m², which was smaller than a basis weight of 42 g/m² of the deodorizing material of the present invention in the deodorizing sheet of Example 5; nevertheless, the deodorizing sheet of Example 4 was comparable in deodorization capabilities to that of Example 5. This confirmed that the deodorizing sheet of the present invention particularly preferably has a density of 0.08 to 0.12 g/cm³ and a thickness of 0.15 to 0.25 mm, and revealed that the deodorizing sheet of the present invention is particularly suitably contained in a seat for a vehicle passenger compartment, specifically in the cover of the seat.

The invention claimed is:

1. A deodorizing material comprising
fibrous activated carbon; and
a component selected from: (A) p-aminobenzoic acid and a sulfate thereof or (B) p-aminobenzoic acid, a sulfate of the p-aminobenzoic acid, and sulfuric acid, said component supported on the fibrous activated carbon,
wherein a total substance amount of the p-aminobenzoic acid and the sulfate of the p-aminobenzoic acid supported per gram of the fibrous activated carbon is 0.94 to 1.31 mmol, and
wherein a ratio of the total substance amount (mmol) of the p-aminobenzoic acid and the sulfate of the p-aminobenzoic acid supported per gram of the fibrous activated carbon relative to a total substance amount (mmol) of the sulfate of the p-aminobenzoic acid and, if present, the sulfuric acid supported per gram of the fibrous activated carbon ([total substance amount of the p-aminobenzoic acid and the sulfate of the p-aminobenzoic acid]÷[total substance amount of the sulfate of the p-aminobenzoic acid and, if present, the sulfuric acid]) is 5.5 to 7.3.

2. A method for producing the deodorizing material according to claim 1, comprising the step of immersing the fibrous activated carbon in a treatment liquid containing an p-aminobenzoic acid and/or a salt thereof, sulfuric acid and/or a salt thereof, and water.

3. A deodorization method for removing an odor of at least one selected from the group consisting of acetaldehyde, ammonia, and toluene, using the deodorizing material according to claim 1.

4. A deodorizing sheet comprising the deodorizing material according to claim 1.

5. The deodorizing sheet according to claim 4, further comprising a binder.

6. The deodorizing sheet according to claim 4, wherein the deodorizing sheet has a density of 0.05 to 0.20 g/cm$^3$ and a thickness of 0.15 to 0.80 mm.

7. The deodorizing material according to claim 1, wherein a total substance amount of the p-aminobenzoic acid and the sulfate of the p-aminobenzoic acid supported per gram of the fibrous activated carbon is 0.94 to 1.09.

* * * * *